United States Patent
Johnson et al.

(10) Patent No.: US 7,163,705 B2
(45) Date of Patent: Jan. 16, 2007

(54) COATED CHEWING GUM PRODUCT AND METHOD OF MAKING

(75) Inventors: Sonya S. Johnson, LaGrange Highlands, IL (US); David G. Barkalow, Deerfield, IL (US); Michael J. Greenberg, Northbrook, IL (US); Gloria T. Sheldon, Hammond, IN (US)

(73) Assignee: Wm. Wrigley Jr. Company, Chicago, IL (US)

( * ) Notice: Subject to any disclaimer, the term of this patent is extended or adjusted under 35 U.S.C. 154(b) by 755 days.

(21) Appl. No.: 10/024,631

(22) Filed: Dec. 17, 2001

(65) Prior Publication Data

US 2002/0164398 A1 Nov. 7, 2002

Related U.S. Application Data

(63) Continuation-in-part of application No. 09/888,057, filed on Jun. 22, 2001, now abandoned, which is a continuation-in-part of application No. 09/621,780, filed on Jul. 21, 2000, now Pat. No. 6,949,264, which is a continuation-in-part of application No. 09/621,643, filed on Jul. 21, 2000, now Pat. No. 6,627,234, which is a continuation of application No. PCT/US99/29792, filed on Dec. 14, 1999, said application No. 09/888,057 is a continuation-in-part of application No. 09/389,211, filed on Sep. 2, 1999, which is a continuation-in-part of application No. 09/308,972, filed on May 27, 1999, which is a continuation-in-part of application No. 09/286,818, filed on Apr. 6, 1999.

(60) Provisional application No. 60/112,389, filed on Dec. 15, 1998.

(51) Int. Cl.
A23G 3/30 (2006.01)
A61K 9/68 (2006.01)

(52) U.S. Cl. ............................. 426/5; 424/48; 424/440; 426/3

(58) Field of Classification Search .................. 426/3, 426/5; 424/48, 440
See application file for complete search history.

(56) References Cited

U.S. PATENT DOCUMENTS

| | | |
|---|---|---|
| 1,298,670 A | 4/1919 | Cramer |
| 1,629,461 A | 5/1927 | Berg et al. |
| 2,892,753 A | 6/1959 | Ludwig |
| 2,990,328 A | 6/1961 | Lincoln |
| 3,011,949 A | 12/1961 | Bilotti |
| 3,029,189 A | 4/1962 | Hardy et al. |
| 3,047,461 A | 7/1962 | Hardy et al. |
| 3,075,884 A | 1/1963 | Bilotti et al. |
| 3,196,172 A | 7/1965 | Wright, Jr. et al. |
| 3,308,022 A | 3/1967 | Cummings et al. |
| 3,498,964 A | 3/1970 | Hayashi |
| 3,554,767 A | 1/1971 | Daum |
| 3,590,057 A | 6/1971 | Suzuki et al. |
| 3,845,217 A | 10/1974 | Ferno et al. |
| 3,877,468 A | 4/1975 | Lichtneckert et al. |
| 3,901,248 A | 8/1975 | Lichtneckert et al. |
| 3,995,064 A | 11/1976 | Ehrgott et al. |
| 4,154,814 A | 5/1979 | Hand et al. |
| 4,238,475 A | 12/1980 | Witzel et al. |
| 4,238,510 A | 12/1980 | Cherukuri et al. |
| 4,250,195 A | 2/1981 | Cherukuri et al. |
| 4,283,408 A | 8/1981 | Hirata et al. |
| 4,317,838 A | 3/1982 | Cherukuri et al. |
| 4,374,858 A | 2/1983 | Glass et al. |
| 4,378,374 A | 3/1983 | Reggio et al. |
| 4,386,063 A | 5/1983 | Boden |
| 4,386,106 A | 5/1983 | Merritt et al. |
| 4,400,372 A | 8/1983 | Muhker et al. |
| 4,446,135 A | 5/1984 | Fountaine |
| 4,452,821 A | 6/1984 | Gergely |
| 4,459,311 A | 7/1984 | DeTora et al. |
| 4,474,749 A | 10/1984 | Kruppa |
| 4,512,968 A | 4/1985 | Komiyama et al. |
| 4,533,556 A | 8/1985 | Piccolo et al. |
| 4,539,315 A | 9/1985 | Bender et al. |
| 4,555,407 A | 11/1985 | Kramer et al. |
| 4,563,345 A | 1/1986 | Arrick |
| 4,639,368 A | 1/1987 | Niazi et al. |
| 4,647,450 A | 3/1987 | Peters et al. |
| 4,711,774 A | 12/1987 | Denick, Jr. et al. |
| 4,716,033 A | 12/1987 | Denick, Jr. |
| 4,737,366 A | 4/1988 | Gergely et al. |
| 4,753,800 A | 6/1988 | Mozda |
| 4,753,805 A | 6/1988 | Cherukuri et al. |
| 4,755,389 A | 7/1988 | Jones et al. |

(Continued)

FOREIGN PATENT DOCUMENTS

DE 43 42 568 6/1984

(Continued)

OTHER PUBLICATIONS

"Flavor Encapsulation Technologies, Flavor Unit Sweet, Product Management", H&R (undated) (published at least before Nov. 27, 1996), 25 pages.

(Continued)

Primary Examiner—Arthur L. Corbin
(74) Attorney, Agent, or Firm—Steven P. Shurtz; Brinks Hofer Gilson & Lione

(57) ABSTRACT

A method for producing a coated chewing gum product with accelerated absorption of medicaments through oral mucosa, as well as the chewing gum product so produced, is obtained by using a xylitol or sorbitol coating, or by adding a water-soluble alkaline material, such as a bicarbonate salt, to the chewing gum center, a coating on the center, or both. Coatings made with sorbitol or xylitol or gum centers that include sodium bicarbonate are particularly preferred.

36 Claims, No Drawings

U.S. PATENT DOCUMENTS

| | | |
|---|---|---|
| 4,758,424 A | 7/1988 | Denick, Jr. et al. |
| 4,822,597 A | 4/1989 | Faust et al. |
| 4,822,816 A | 4/1989 | Markham |
| 4,828,820 A | 5/1989 | Glass et al. |
| 4,832,994 A | 5/1989 | Fey |
| 4,835,162 A | 5/1989 | Abood |
| 4,835,188 A | 5/1989 | Ho et al. |
| 4,849,227 A | 7/1989 | Cho |
| 4,853,212 A | 8/1989 | Faust et al. |
| 4,867,989 A | 9/1989 | Silva et al. |
| 4,882,152 A | 11/1989 | Yang et al. |
| 4,894,234 A | 1/1990 | Sharma et al. |
| 4,908,211 A | 3/1990 | Paz |
| 4,908,212 A | 3/1990 | Kwon et al. |
| 4,929,447 A | 5/1990 | Yang |
| 4,929,508 A | 5/1990 | Sharma et al. |
| 4,933,184 A | 6/1990 | Tsuk |
| 4,935,242 A | 6/1990 | Sharma et al. |
| 4,938,963 A | 7/1990 | Parnell |
| 4,944,949 A | 7/1990 | Story et al. |
| 4,963,369 A | 10/1990 | Song et al. |
| 4,968,511 A | 11/1990 | D'Amelia et al. |
| 4,968,716 A | 11/1990 | Markham |
| 4,971,079 A | 11/1990 | Talapin et al. |
| 4,971,787 A | 11/1990 | Cherukuri et al. |
| 4,975,270 A | 12/1990 | Kehoe |
| 4,978,537 A | 12/1990 | Song |
| 4,997,659 A | 3/1991 | Yatka et al. |
| 5,013,716 A | 5/1991 | Cherukuri et al. |
| 5,015,464 A | 5/1991 | Strobridge |
| 5,045,325 A | 9/1991 | Lesko et al. |
| 5,070,085 A | 12/1991 | Markham |
| 5,110,608 A | 5/1992 | Cherukuri |
| 5,124,156 A | 6/1992 | Shibata et al. |
| 5,126,151 A | 6/1992 | Bodor et al. |
| 5,139,787 A | 8/1992 | Broderick et al. |
| 5,139,794 A | 8/1992 | Patel et al. |
| 5,154,927 A | 10/1992 | Song et al. |
| 5,156,842 A | 10/1992 | Mulligan |
| 5,179,122 A | 1/1993 | Greene et al. |
| 5,182,099 A | 1/1993 | Jonsson et al. |
| 5,229,137 A | 7/1993 | Wolfe |
| 5,244,670 A | 9/1993 | Upson et al. |
| 5,262,179 A | 11/1993 | Gregory et al. |
| 5,284,657 A | 2/1994 | Lu et al. |
| 5,286,500 A | 2/1994 | Synosky et al. |
| 5,294,433 A | 3/1994 | Singer et al. |
| 5,294,449 A | 3/1994 | Greenberg |
| 5,340,566 A | 8/1994 | Curtis et al. |
| 5,378,131 A | 1/1995 | Greenberg |
| 5,380,530 A * | 1/1995 | Hill ............. 424/440 |
| 5,380,535 A | 1/1995 | Geyer et al. |
| 5,397,580 A | 3/1995 | Song et al. |
| 5,410,028 A | 4/1995 | Asami et al. |
| 5,419,919 A | 5/1995 | Song et al. |
| 5,433,960 A | 7/1995 | Meyers |
| 5,445,834 A | 8/1995 | Burger et al. |
| 5,455,286 A | 10/1995 | Amidon et al. |
| 5,456,677 A | 10/1995 | Spector |
| 5,487,902 A * | 1/1996 | Andersen et al. ............. 426/3 |
| 5,488,962 A | 2/1996 | Perfetti |
| 5,494,685 A | 2/1996 | Tyrpin et al. |
| 5,496,541 A | 3/1996 | Cutler |
| 5,512,306 A | 4/1996 | Carlsson et al. |
| 5,523,097 A | 6/1996 | Song et al. |
| 5,534,272 A | 7/1996 | Bernstein |
| 5,536,511 A | 7/1996 | Yatka |
| 5,543,160 A | 8/1996 | Song et al. |
| 5,554,380 A | 9/1996 | Cuca et al. |
| 5,569,477 A | 10/1996 | Nesbitt |
| 5,571,528 A | 11/1996 | Lee et al. |
| 5,571,543 A | 11/1996 | Song et al. |
| 5,576,344 A | 11/1996 | Sandler et al. |
| 5,580,590 A | 12/1996 | Hartman |
| 5,582,855 A | 12/1996 | Cherukuri et al. |
| 5,585,110 A | 12/1996 | Kalili et al. |
| 5,593,685 A | 1/1997 | Bye et al. |
| 5,601,858 A | 2/1997 | Manshukhani |
| 5,605,698 A | 2/1997 | Ueno |
| 5,607,697 A | 3/1997 | Alkire et al. |
| 5,618,517 A | 4/1997 | Miskewitz |
| 5,628,986 A | 5/1997 | Sanker et al. |
| 5,629,013 A | 5/1997 | Davis |
| 5,629,026 A | 5/1997 | Davis |
| 5,629,035 A | 5/1997 | Miskewitz |
| 5,645,853 A | 7/1997 | Winston et al. |
| 5,651,987 A | 7/1997 | Fuisz |
| 5,656,652 A | 8/1997 | Davis |
| 5,665,386 A | 9/1997 | Bebet et al. |
| 5,665,406 A | 9/1997 | Reed et al. |
| 5,667,802 A | 9/1997 | Grimberg |
| 5,693,334 A | 12/1997 | Miskewitz |
| 5,698,215 A | 12/1997 | Kalili et al. |
| 5,702,687 A | 12/1997 | Miskewitz |
| 5,711,961 A | 1/1998 | Kalili et al. |
| 5,716,928 A | 2/1998 | Benet et al. |
| 5,720,974 A | 2/1998 | Makino et al. |
| 5,736,175 A | 4/1998 | Cea et al. |
| 5,744,164 A | 4/1998 | Chauffard et al. |
| 5,753,255 A | 5/1998 | Chavkin et al. |
| 5,756,074 A | 5/1998 | Ascione et al. |
| 5,780,046 A | 7/1998 | Humber et al. |
| 5,800,847 A | 9/1998 | Song et al. |
| 5,824,291 A | 10/1998 | Howard |
| 5,834,002 A | 11/1998 | Athanikar |
| 5,846,557 A | 12/1998 | Eisenstadt et al. |
| 5,854,267 A | 12/1998 | Berlin et al. |
| 5,858,383 A | 1/1999 | Precopio |
| 5,858,412 A | 1/1999 | Staniforth et al. |
| 5,858,413 A | 1/1999 | Jettka et al. |
| 5,858,423 A | 1/1999 | Yajima et al. |
| 5,866,179 A | 2/1999 | Testa |
| 5,877,173 A | 3/1999 | Olney et al. |
| 5,882,702 A | 3/1999 | Abdel-Malik |
| 5,889,028 A | 3/1999 | Sandborn et al. |
| 5,889,029 A | 3/1999 | Rolf |
| 5,897,891 A | 4/1999 | Godfrey |
| 5,900,230 A | 5/1999 | Cutler |
| 5,912,007 A | 6/1999 | Pan et al. |
| 5,912,030 A | 6/1999 | Huziinec et al. |
| 5,916,606 A | 6/1999 | Record et al. |
| 5,922,346 A | 7/1999 | Hersh |
| 5,922,347 A | 7/1999 | Häusler et al. |
| 5,928,664 A | 7/1999 | Yang et al. |
| 5,958,380 A | 9/1999 | Winston et al. |
| 5,958,472 A | 9/1999 | Robinson et al. |
| 5,980,955 A | 11/1999 | Grennberg et al. |
| 5,989,588 A | 11/1999 | Korn et al. |
| 6,024,988 A | 2/2000 | Ream et al. |
| 6,043,244 A | 3/2000 | Caruso |
| 6,066,342 A | 5/2000 | Gurol et al. |
| 6,077,524 A | 6/2000 | Bolder et al. |
| 6,077,536 A | 6/2000 | Merrifield et al. |
| 6,090,412 A | 7/2000 | Hashimoto et al. |
| 6,165,516 A | 12/2000 | Gudas et al. |
| 6,200,604 B1 | 3/2001 | Pather et al. |
| 6,221,402 B1 | 4/2001 | Itoh |
| 6,258,376 B1 | 7/2001 | Athanikar |
| 6,290,985 B1 | 9/2001 | Ream et al. |
| 6,303,159 B1 | 10/2001 | Barkalow et al. |
| 6,322,806 B1 | 11/2001 | Ream et al. |
| 6,350,480 B1 | 2/2002 | Urnezis et al. |
| 6,355,265 B1 | 3/2002 | Ream et al. |
| 6,465,003 B1 | 10/2002 | Ream et al. |

| | | |
|---|---|---|
| 6,531,114 B1 | 3/2003 | Gmunder et al. |
| 6,537,525 B1 | 3/2003 | West |
| 6,558,692 B1 | 5/2003 | Ream et al. |
| 2001/0002998 A1 | 6/2001 | Ream et al. |
| 2001/0036445 A1 | 11/2001 | Athanikar |
| 2002/0012633 A1 | 1/2002 | Gmunder et al. |
| 2002/0022057 A1 | 2/2002 | Battery et al. |
| 2002/0039560 A1 | 4/2002 | Ream et al. |
| 2002/0159956 A1 | 10/2002 | Ream et al. |

FOREIGN PATENT DOCUMENTS

| | | |
|---|---|---|
| EP | 0 202 819 A2 | 11/1986 |
| EP | 0 217 109 A2 | 4/1987 |
| EP | 0 221 850 A2 | 5/1987 |
| EP | 0 239 541 A2 | 9/1987 |
| EP | 0 371 584 A2 | 6/1990 |
| EP | 0 273 809 B1 | 7/1998 |
| FR | 2 345 938 | 10/1977 |
| FR | 2 635 441 | 2/1990 |
| FR | 2 706 771 | 6/1993 |
| GB | 0 934 596 | 8/1963 |
| GB | 0 963 518 | 7/1964 |
| GB | 1 489 832 | 10/1977 |
| GB | 2 181 646 A | 4/1987 |
| IT | 02173487 | 7/1997 |
| IT | 01293655 | 3/1999 |
| JP | 91-11240 | 5/1991 |
| JP | 91-251533 | 11/1991 |
| JP | 94-303911 | 11/1994 |
| JP | 96-19370 | 1/1996 |
| JP | 86/242561 | 10/1996 |
| JP | 2000-159691 | 6/2000 |
| KR | 94-2868 | 4/1994 |
| WO | WO 84/02271 | 6/1984 |
| WO | WO 90/12511 | 11/1990 |
| WO | WO 90/12583 | 11/1990 |
| WO | WO 92/06680 | 4/1992 |
| WO | WO 95/00038 | 1/1995 |
| WO | WO 95/00039 | 1/1995 |
| WO | WO 95/10290 | 4/1995 |
| WO | WO 96/00070 | 1/1996 |
| WO | WO 96/03975 | 2/1996 |
| WO | WO 97/21424 | 6/1997 |
| WO | WO 97/24036 | 6/1997 |
| WO | 98/23165 | * 6/1998 |
| WO | WO 98/23165 | 6/1998 |
| WO | WO 98/23166 | 6/1998 |
| WO | WO 98/23167 | 6/1998 |
| WO | WO 99/27798 | 6/1998 |
| WO | WO 99/44436 | 9/1998 |
| WO | WO 99/33352 | 7/1999 |
| WO | WO 00/13523 | 3/2000 |
| WO | WO 00/35296 | 6/2000 |
| WO | WO 00/35298 | 6/2000 |
| WO | WO 00/38532 | 7/2000 |
| WO | WO 02/13781 A1 | 2/2002 |

OTHER PUBLICATIONS

Dr. Massimo Calanchi and Dr. Sam Ghanta, "Taste-masking of oral formulations", *Eurand International SpA, Pharmaceutical Manufacturing International*, 1996, 5 pages.

The Eurand Group, Brochure (undated) (published at least before Nov. 27, 1996), 16 pages.

Merck Index, 11th Ed., #1635 "Caffeine" (1989), p. 248.

Merck Index, 12th Ed., #2337 "Cimetidine" (1996), p. 383.

Merck Index, 12th Ed., #3264 "Dimethicone" (1996), p. 544.

Merck Index, 12th Ed., #3972 "Famotidine" (1996), p. 667.

Merck Index, 12th Ed., #6758 "Nizatidine" (1996), p. 1143.

Merck Index, 12th Ed., #6977 "Omeprazole" (1996), p. 1174.

Merck Index, 12th Ed., #8272 "Rabeprazole" (1996), p. 1392.

Merck Index, 12th Ed., #8286 "Ranitidine" (1996), p. 1395.

James G. Elliot, "Application of Antioxidant Vitamins in Foods and Beverages" *Food Technology*, (Feb. 1999), pp. 46-48.

C. Curtis Vreeland, "Nutraceuticals Fuel Confectionery Growth" *Candy R& D*, (Mar. 1999), pp. 29, 31-32, 34-35.

Kitty Broihier, R.D., "Foods of Tomorrow, Milking The Nutrition Marker", *Food Processing*, (Mar. 1999), pp. 41, 42 and 44.

Kitty Broihier, R.D., "Tea Time For Nutraceuticals, New Black, Green Tea Products Brew Up a Bevy Of Health Benefits", *Food Processing*; (Mar. 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar. 1999).

Product package "Aspergum" distributed by Heritage Consumer Products, LLC (on sale prior to Nov. 27, 1995).

Product package "Chew & Sooth Zinc Dietary Supplement Gum" by Gumtech International, Inc. (undated) (on sale prior to Nov. 27, 1995).

Product package "Dental Care the Baking Soda Gum" distributed by Church & Dwight Co., Inc. (1998).

Product package "BreathAsure Dental Gum" distributed by Breath Asure, Inc. (1998).

Product package "Trident Advantage with Baking Soda" distributed by Warner-Lambert Co. (1998).

Product package "CHOOZ Antacid/Calcium Supplement with Calcium Carbonate" distributed by Heritage Consumer Products Co.

Hertiage Consumer Products Co. article from the Internet "Cosmetics and Toiletries, The Heritage Story", printed Jul. 20, 2000, <http://www/cnewsusa.com/Connecticut/14997.html>, 1 page.

The United States Pharmacopeia The National Formulary—"General Information", dated Jan. 1, 1990 pp. 1624-1625 and pp. 1696-1697.

Gumtech article from the Internet "Customized Solutions For Customer Brands", printed Oct. 18, 2000, <http://www.gum-tech.com/cus-brands.html>, 3 pages.

Product package for Stay Alert Caffeine Supplement Gum, distributed by Amurol Confections Company (first quarter 1998).

Rabeprazole article from the Internet "Rabeprazole: Pharmacokinetics and Safety in the Elderly", printed Sep. 22, 2000,<http://www.mmhc.com/cg/articles/CG9905/Hum-phries.html>, 2 pages.

Brochure for "Minerals Technolgies Specialty Minerals", 1998, 19 pages.

Akitoshi et al., Abstract "Acceleration of Transdermal Absorption of Pharmaceuticals by Essential Oils and Organic Solvents," Chem. Abst., 112:125228t, 1990.

Beckett, A. H. et al., "Buccal absorption of basis drugs and its application as an *in vivo* model of passive drug transfer through lipid membranes", *J. Pharm. Pharmac., 19 Suppl*, 1967, pp. 31S-41S.

Bradford, A Rapid and Sensitive Method for the Quantification of Microgram Quantities of Protein Utilizing the Principle of Protein-Dye Binding, Analytical Biochemistry, 72:248-254 (1976).

Nielsen et al., P-Glycoprotein as Multidrug Transporter: A Critical Review of Current Multidrug Resistant Cell Lines, Chimica et Biophysica Acta., 1139:169-183 (1992).

Adams, M.W., d-Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2-4, 1992.

Chang, Tammy et al., "The Effect of Water-Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453-457.

Kronbach, Thomas et al.; "Oxidation of Midazolam and Triazolam by Human Liver Cytochrome P450lllA4" (1989) *Molec. Pharm.* 36:89-96.

Lalka et al.; "The Hepatic First-Pass Metabolism of Problematic Drugs" (1993) *J. Clin. Pharmacol.* 33:657-669.

Lum et al.; "Clinical Trials of Modulation of Multidrug Resistance. Pharmacokinetic and Pharmacodynamic Considerations" (1993) *Cancer* 72:3502-3514.

Muranishi, Shozo; "Absorption Enhancers" (1990) *Crit. Rev. Ther. Drug Carrier Sys.*, 7:1-33.

Somberg et al.; "The Clinical Implications of First-Pass Metabolism: Treatment Strategies for the 1990's" (1993) *J. Clin. Pharmacol.* 33:670-673.

Tam, Yun K.; "Individual Variation in First-Pass Metabolism" (1993) *Clin. Pharmacokinet.* 25:300-328.

Van Hoogdalem et al.; "Intestinal Drug Absorption Enhancement: An Overview" (1989) *Pharmacol. Ther.* 44:407-443.

Warren et al.; "Increased Accumulation of Drugs in Multidrug-Resistant Cell Induced by Liposomes" (1992) *Cancer Research* 52:3241-3245.

Watkins, Paul B.; "The Role of Cytochromes P-450 in Cyclosporine Metabolism" (1990) *J. Am. Acad. Dermacol.* 23:1301-1309.

Weinberg, David S. et al. "Sublingual absorption of selected opioid analgesics", *Clin. Pharmacol Ther.*, 1998, vol. 44, pp. 335-342.

Wrighton et al.; "In Vitro Methods for Assessing Human Hepatic Drug Metabolism: Their Use in Drug Development" (1993) 25:453-484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical-Chemical Properties Shared by Compounds that Modulate Multidrug Resistance in Human Loukemic Cells" (1988) *Molec. Pharmacol.* 33:454-462.

U.S. Appl. No. 09/286,818, filed Apr. 6, 1999.
U.S. Appl. No. 09/421,905, filed Oct. 20, 1999.
U.S. Appl. No. 09/510,878, filed Feb. 23, 2000.
U.S. Appl. No. 09/535,458, filed Mar. 24, 2000.
U.S. Appl. No. 09/552,290, filed Apr. 19, 2000.
U.S. Appl. No. 09/591,256, filed Jun. 9, 2000.
U.S. Appl. No. 09/592,400, filed Jun. 13, 2000.
U.S. Appl. No. 09/618,808, filed Jul. 18, 2000.
U.S. Appl. No. 09/621,780, filed Jul. 21. 2000.
U.S. Appl. No. 09/621,643, filed Jul. 21, 2000.
U.S. Appl. No. 09/631,326, filed Aug. 3, 2000.
U.S. Appl. No. 09/651,514, filed Aug. 30, 2000.
U.S. Appl. No. 09/653,669, filed Sep. 1, 2000.
U.S. Appl. No. 09/654,464, filed Sep. 1, 2000.
U.S. Appl. No. 09/671,552, filed Sep. 27, 2000.
U.S. Appl. No. 09/714,571, filed Nov. 16, 2000.
U.S. Appl. No. 09/747,300, filed Dec. 22, 2000.
U.S. Appl. No. 09/747,323, filed Dec. 22, 2000.
U.S. Appl. No. 09/748,699, filed Dec. 22, 2000.
U.S. Appl. No. 09/749,983, filed Dec. 27, 2000.
U.S. Appl. No. 09/759,561, filed Jan. 11, 2001.
U.S. Appl. No. 09/759,838, filed Jan. 11, 2001.
U.S. Appl. No. 09/681,935, filed Jun. 28, 2001.
U.S. Appl. No. 09/924,914, filed Aug. 8, 2001.
U.S. Appl. No. 09/955,870, filed Sep. 19, 2001.
U.S. Appl. No. 09/956,445, filed Sep. 19, 2001.
U.S. Appl. No. 09/990,628, filed Nov. 13, 2001.
U.S. Appl. No. 09/992,122, filed Nov. 13, 2001.
U.S. Appl. No. 10/024,631, filed Dec. 17, 2001.
U.S. Appl. No. 10/044,113, filed Jan. 9, 2002.

"Goody's Extra Strength Headache Powder", printed from the Internet at: http//www.epinions.com/contant_98033045124, dated Mar. 11, 2004, 3 pages.

Remington, Joseph. P., *The Science and Practice of Pharmacy*, 19th Edition, copyright 1995, pp. 710, 1231-1232 and 1383-1392.

\* cited by examiner

COATED CHEWING GUM PRODUCT AND METHOD OF MAKING

REFERENCE TO EARLIER FILED APPLICATIONS

The present application is a continuation-in-part of U.S. patent application Ser. No. 09/888,057, filed Jun. 22, 2001, now abandoned which is continuation-in-part of the following: (1) U.S. patent application Ser. No. 09/621,780, filed Jul. 21, 2000, now U.S. Pat. No. 6,949,264 which is a continuation of PCT Application Ser. No. US99/29792, filed Dec. 14, 1999, which designated the United States, said PCT application being a continuation-in-part of U.S. patent application Ser. No. 09/389,211, filed Sep. 2, 1999, a continuation-in-part of U.S. patent application Ser. No. 09/286,818, filed Apr. 6, 1999 and a continuation-in-part of U.S. patent application Ser. No. 09/308,972, filed May 27, 1999, which is a nationalization of PCT/US96/18977, filed Nov. 27, 1996; (2) U.S. patent application Ser. No. 09/552,290, filed Apr. 19, 2000, which is a continuation of U.S. patent application Ser. No. 09/389,211, filed Sep. 2, 1999, which in turn claims the benefit of the filing date under 35 U.S.C. §119(e) of U.S. Provisional Application Ser. No. 60/112,389, filed Dec. 15, 1998; and (3) U.S. patent application Ser. No. 09/621,643, filed Jul. 21, 2000, now U.S. Pat. No. 6,627,234 which is a continuation of PCT Application Ser. No. US99/29742, filed Dec. 14, 1999, which designated the United States, said PCT application being a continuation-in-part of U.S. patent application Ser. No. 09/389,211, filed Sep. 2, 1999, a continuation-in-part of U.S. patent application Ser. No. 09/286,818, filed Apr. 6, 1999 and a continuation-in-part of U.S. patent application Ser. No. 09/308,972, filed May 27, 1999, which is a nationalization of PCT/US96/18977, filed Nov. 27, 1996.

Each of the foregoing applications are hereby incorporated by reference.

BACKGROUND OF THE INVENTION

The present invention relates to the composition of, and methods of producing, a coated chewing gum product containing an effective amount of a medicament. The inventive composition accelerates the absorption of the medicament through the oral mucosa.

It is of course known to provide active medicaments to individuals for various purposes. These medicaments can be used to treat diseases and as such are typically referred to as drugs or medicaments. Likewise, the drugs or medicaments can be used for preventive purposes. Still, it is known to provide medicaments to an individual for a variety of non-medical purposes including enhancing performance or maintaining health.

There are a great variety of such medicaments. These medicaments run the gamut from stimulants such as caffeine to drugs such as analgesics, tranquilizers, and cardiovascular products, as well as vitamins, minerals, and supplements. Some such medicaments are taken on an "as-needed" basis while other medicaments must be taken at regular intervals by the individual.

Typically, drugs or medicaments are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Oral administration of drugs is by far the most common method of moving drugs towards systemic circulation. When administered orally, drug absorption usually occurs due to the transport across the membranes of the epithelial cells within the gastrointestinal tract. Absorption after oral administration is confounded by numerous factors. These factors include differences down the alimentary cannel in: the luminal pH; surface area per luminal volume; perfusion of tissue, bile, and mucus flow; and the epithelial membranes. See *Merck Manual* at page 2599.

A further issue affecting the absorption or orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that affect the dissolution rate and therefore determine the availability of the drug for absorption. See *Merck Manual* at page 2600.

When a drug rapidly dissolves from a drug product and readily across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailabilities owning to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically parenteral administration requires the use of medical personnel and is just not warranted nor practical for the administration of most agents and drugs, e.g., analgesics. Even when required, parenteral administration is objectionable due to patient concerns including comfort, infection, etc., as well as the equipment and costs involved.

It is known to incorporate medicaments into chewing gums for the purpose of providing an opportunity for the medicament to be absorbed through mucous membranes in the mouth. For example, U.S. Pat. No. 4,639,368 to Niazi discloses chewing gum compositions containing orally administrable medicament capable of being absorbed through the buccal cavity. Such systems have the advantage that the medicament is absorbed directly into the bloodstream. Increasing the rate of this absorption would further enhance the benefit of delivering medicaments using chewing gum.

Earlier patent applications owned by Applicants' assignee disclose such enhanced systems, which are more fully explored in the present application. It was earlier discovered that it is particularly advantageous to formulate a medicinal gum product as a coated chewing gum with a pharmaceutical agent in the coating to overcome the tendency for the agent to be entrapped in the gum base. Grandparent Application PCT/US99/29742, published as WO 00/35296, discloses adding an active agent to the coating of chewing gum. The active agent may be added to the coating solution and can be premixed with a flavor or solvent. The active agent may be added to the coating along with transdermal enhancing agents to increase transmucosal absorption.

Grandparent Application PCT/US99/29792, published as WO 00/35298, discloses a method for producing a chewing gum with a controlled release of an active agent by encapsulating the active agent. The use of sodium bicarbonate in a chewing gum containing a medicament, to increase the buccal/lingual absorption of the medicament into the bloodstream by raising the pH of the saliva, is also discussed.

SUMMARY OF THE INVENTION

In a first aspect, the present invention is a coated chewing gum product including a medicament comprising: a chewing gum center; a chewing gum coating containing at least one medicament; and a water-soluble alkaline material incorporated into the chewing gum center, the coating, or both.

In a second aspect, the present invention is a method of delivering a medicament with accelerated absorption through the oral mucosa comprising the steps of: providing a chewing gum center; coating the chewing gum center with a coating comprising a polyol selected from the group consisting of xylitol and sorbitol, and containing at least one medicament; either the chewing gum center, the coating, or both incorporating a bicarbonate salt; and causing an individual in need of the medicament to chew the product.

In a third aspect, the present invention is a coated chewing gum product with absorption acceleration of caffeine, comprising a chewing gum center comprising a gum base, a flavor, and a bulking/sweetening agent; and a chewing gum coating comprising caffeine and a polyol selected from the group consisting of sorbitol and xylitol.

In preferred embodiments, using xylitol or sorbitol as the coating material and adding 0.1% to 1% sodium bicarbonate to the center, or coating, of a chewing gum with a systemic drug in the coating, significant increases in absorption of the drug through oral mucosa can be achieved. The enhanced absorption due to the use of sorbitol or xylitol is an unexpected result. The enhanced absorption due to the presence of a water-soluble alkaline material in the chewing gum product is also an unexpected result. It is possible that other coating polyols and other food acceptable alkaline agents might provide similar benefits.

DETAILED DESCRIPTION OF THE PREFERRED EMBODIMENTS OF THE INVENTION

As noted above, previous applications assigned to the assignee of the present application disclose that it is particularly advantageous to formulate a medicinal gum product as a coated chewing gum product with the pharmaceutical agent in the coating to overcome the tendency for the agent to be entrapped in the gum base.

It has now been discovered that certain enhancements in the formulation of such products can further increase the rate at which the medicament drug passes through the mucous membranes of the oral cavity and into the bloodstream. It has been confirmed that the addition of a water-soluble alkaline material, preferably a bicarbonate salt like sodium bicarbonate, to the center of the gum further increases the absorbance rate. It is believed that the water-soluble alkaline material raises the pH of the oral cavity to a range in which at least certain drugs are more rapidly absorbed through the oral mucosa.

Additionally, it has been discovered that the use of sorbitol or xylitol instead of maltitol as the primary coating material increases the absorption rate dramatically, particularly sorbitol has been found to increase the absorption of caffeine. It is believed that the physical characteristics of coating made from the inventive materials provide the greatest opportunity for the drug to be absorbed through the oral mucosa. Specifically, the preferred coating texture and solubility are such that, when chewed, it breaks quickly into small pieces that are readily dissolved in the mouth, rather than being swallowed or chewed into the gum mass where the drug may become bound in the gum base.

The level of water-soluble alkaline material in the preferred chewing gum center may vary according to the size of the pellet, the chemical nature of the pharmaceutical agent, the rate of absorption desired and sensory considerations. Generally from about 0.01 to about 2% water-soluble alkaline material is present in the gum product. In an embodiment, 0.1 to 1% water-soluble alkaline material is present in the gum product. More preferably, 0.3 to 0.7% water-soluble alkaline material is present in the gum product. The water-soluble alkaline material may be present in the center, the coating, or both. In a preferred embodiment, about 0.4 to 0.6% sodium bicarbonate is present in the gum center.

In order to maximize the effectiveness of absorbance through the oral mucosa, it is necessary to maximize the percentage of the total drug that is absorbed rather than swallowed. For this reason it is preferred that both discoveries associated with the invention be used in combination. Hence, a preferred embodiment of the invention is a product with a sorbitol or xylitol coating and sodium bicarbonate in the gum center or coating.

As the chewing gum is chewed, the medicament in the coating is released into the saliva quickly. During continual chewing, the medicament in the saliva may be then forced, due to the pressure created by the chewing gum, through the oral mucosa in the buccal cavity. The oral mucosa favors drug absorption. In contrast to a typical orally ingested drug, wherein the solution is in contact too briefly for absorption to be appreciable through the oral mucosa, it is believed that during the chewing, the medicament remains in the buccal cavity and may be forced or partitioned through the oral mucosa. An increase in the transmucosal absorption of the drug may be achieved as well as an increase in the bioavailability of the drug as compared to typical oral administration. The medicament may be absorbed much quicker than if it was swallowed as in a typical oral administration. Indeed, the absorption approaches that of a parental administration and bioavailability may be also much greater than oral administration.

It is also possible that less medicament can be placed in the chewing gum coating than is typically orally administered to an individual to achieve an effect and the same bioequivalence can be achieved. In some instances, for certain drugs and agents, the administration of the medicament using chewing gum through the buccal activity may provide an increase in therapeutic effect even as compared to parenteral administration.

By the term "medicament" the present invention refers to a compound that has a desired therapeutic or physiological effect once ingested and/or metabolized. The therapeutic effect may be one which decreases the growth of a xenobiotic or other gut flora or fauna, alters the activity of an enzyme, provides the physical relief from a malady (e.g., diminishes pain, acid reflux or other discomfort), has an effect on the brain chemistry of molecules that determine mood and behavior. Of course these are just examples of what is intended by therapeutic effect. Those of skill in the art will readily recognize that a particular agent has or is associated with a given therapeutic effect.

The medicament may be any agent that is traditionally used as a medicament and lends itself to being administered through the oral cavity. Such active agents may be vitamins, cancer therapeutics, antimycotics, oral contraceptives, nicotine or nicotine replacement agents, minerals, analgesics, antacids, muscle relaxants, tranquilizers, antihistamines, decongestants, anesthetics, antitussives, diuretics, anti-inflammatories, antimicrobial agents, HIV medications, AIDS medications, neurological drugs, antivirals, psychotherapeutic agents, anti-diabetic agents, cardiovascular agents, bioengineered pharmaceuticals, nutraceuticals and nutritional supplements. Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K.

Examples of cancer therapeutic agents include but are not limited to cisplatin (CDDP), procarbazine, mechlorethamine, cyclophosphamide, camptothecin, ifosfamide, melphalan, chlorambucil, bisulfan, nitrosurea, dactinomycin: daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriaxoxone, cefotaxime, chloramphenicol, clavunate, sulbactam, probenecid, doxycycline, spectinomycin, cefixime, penicillin G, minocycline, P-lactamase inhibitors; meziocillin, piperacillin, aztreonam, norfloxacin, trimethoprim, ceftazidime and dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscamet, ganciclovir, zidovudine, dideoxycytosine, dideoxyinosine, stavudine, famciclovir, didanosine, zalcitabine, rifimantadine, and cytokines.

Antacids include cimetidine, ranitidine, nizatidine, famotidine, omeprazole, bismuth antacids, metronidazole antacids, tetracylcine antacids, clarthromycin antacids, hydroxides of aluminum, magnesium, sodium bicarbonates, calcium bicarbonate and other carbonates, silicates, and phosphates.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan hydrobromide, levopropoxyphene napsylate, noscapine, carbetapentane, caramiphen, chlophedianol, pseudoephedrine hydrochloride, pseudoephedrine sulfate, phenylephidrine, diphenhydramine, glaucine, pholcodine, and benzonatate.

Anesthetics include etomidate, ketamine, propofol, and benodiazapines (e.g., chlordiazepoxide, diazepame, clorezepate, halazepam, flurazepam, quazepam, estazolam, triazolam, alprozolm, midazolam, temazepam, oxazepam and lorazepam), benzocaine, dyclonine, bupivacaine, etidocaine, lidocaine, mepivacaine, promoxine, prilocaine, procaine, proparcaine, ropivacaine and tetracaine. Other useful agents may include amobartital, aprobarbital, butabarbital, butalbital mephobarbital, methohexital, pentobarbital, phenobarbital, secobarbital, thiopental, paral, chloralhydrate, ethchlorvynol, clutethimide, methprylon, ethinamate, and meprobarnate.

Analgesics include opioids and other medicaments such as morphine, mepidine, dentanyl, sufentranil, alfentanil, aspirin, acetaminophen, ibuprofen, indomethacine, naproxen, atrin, isocome, midrin, axotal, firinal, phrenilin, ergot, and ergot derivatives (wigraine, cafergot, ergostat, ergomar, dihydroergotamine), imitrex, and ketoprofen.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprion olactone, canrenone, and potassium canrenoate.

Anti-inflammatories include but are not limited to salicylic acid derivatives (e.g. aspirin), indole and indene acetic acids (indomethacin, sulindac and etodalac), heteroaryl acetic acids (tolmetin diclofenac and ketorolac), aryl propionic acid derivatives (ibuprofen, naproxen, ketoprofen, fenopren, and oxaprozine), anthranilic acids (mefenamic acid and meclofenamic acid) and enolic acids (piroxicam, tenoxicam, phenylbutazone and oxyphenthatrazone).

Psychotherapeutic agents include thorazine, serentil, mellaril, millazinetindal, permitil, prolixin, trilafon, stelazine, suprazine, taractan, navan, clozaril, haldol, halperon, loxitane, moban, orap, risperdal, alprazolam, chordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, wellbutrin, serzone, desyrel, nardil, parnate and eldepryl.

Cardiovascular agents include but are not limited to nitroglycerin, isosorbide dinitrate, sodium nitroprisside, captopril, enalaprill, enalaprilat, quinapril, lisinopril, ramipril, losartan, amrinone, linnone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine, or a sexual dysfunction agent like sildenafil citrate (Viagra).

It is envisioned that depending on the medicament, the resultant chewing gum can be used to treat inter alia: coughs, colds, motion sickness; allergies; fevers; pain; inflammation; sore throats; cold sores; migraines; sinus problems; diarrhea; diabetes, gastritis; depression; anxiety, hypertension; angina and other maladies and symptoms. Also these gums may be useful in ameliorating cravings in substance abuse withdrawal or for appetite suppression. Specific medicaments include by way of example and limitation: caffeine, aspirin, acetaminophen; ibuprofen; ketoprofen; cimetidine, ranitidine, famotidine, dramamine, omeprazole, dyclonine hydrochloride, chlorpheniramine maleate, pseudoephedrine hydrochloride, dextromethorphan hydrobromide, benzocaine, sodium naproxen, and nicotine.

Compositions that may be formulated into a suitable chewing gum formulation are described in, for examples, U.S. Pat. No. 5,858,423; U.S. Pat. No. 5,858,413; U.S. Pat. No. 5,858,412 and U.S. Pat. No. 5,858,383. Additionally, Goodman and Gilman's "The Pharmaceutical Basis of Therapeutics" (Eds. Hardman et al., Publ. McGraw Hill, N.Y.) provides comprehensive guidance of useful drugs and their mechanisms of action. Medicated chewing gums have been particularly effective in the delivery of agents such as nicotine as described in, for example, U.S. Pat. No. 5,866,179; and U.S. Pat. No. 5,889,028. U.S. Pat. No. 5,846,557 describes general chewing gum compositions containing cough suppressing agents. These patents are incorporated herein by reference as providing a teaching of the incorporation of medicinal agents into oral chewable formulations. It should be understood that the present chewing gum formulation(s) and coatings are not limited to the agents listed herein above, indeed any medicament that lends itself to ingestion may be formulated into the chewing gum coatings and used in the present invention.

Nutraceuticals and nutritional supplements may also be added to chewing gums as well as the gum coatings as active agents. Among these are herbs and botanicals that include, but are not limited to capsicum, chamomile, cat's claw, echinacea, garlic, ginger, ginko, various ginseng, green tea, golden seal, kava kava, nettle, passion flower, saw palmetto, St. John's wort, and valerian. Also included are mineral supplements such as calcium, copper, iodine, iron, magnesium, manganese, molybdenum, phosphorous, selenium and zinc. Other nutraceuticals that also can be added to chewing gum as active agents are benzoin, fructo-oligosaccharides, glucosamine, grapeseed extract, guarana, inulin, phosphotidylserine, phytosterols, phytochemicals, isoflavones, lecithin, lycopene, oligofructose, polyphenol and psyllium, as well as weight loss agents such as chromium picolinate and phenylpropanolamine.

Pursuant to the present invention, depending on the medicament, the dosing regiment will change. For example, if the medicament is an analgesic, the chewing gum product would be taken on an "as-needed" basis. Of course, similar to the oral administration of an analgesic, there would be restrictions on the number of pieces of chewing gum product chewed, for example, not more often than one pellet every four hours and not more often than four to five times a day. If the agent is a stimulant such as caffeine to be used to enhance performance than the chewing gum product would be chewed, in a preferred embodiment ten minutes or less before the performance.

The medicament can be contained in coatings on a variety of different chewing gum compositions. Referring now to the chewing gum, pursuant to the present invention the chewing gum may be based on a variety of different chewing gums that are known. For example, the chewing gums can be low or high moisture, sugar or sugarless, wax containing or wax free, low calorie (via high base or low calorie bulking agents), and/or may contain dental agents.

Medicaments may be added to the gum coating along with sweeteners, more specifically high-intensity sweeteners such as thaumatin, dihydrochalcones, acesulfame K, aspartame, N-substituted APM derivatives such as neotame, sucralose, alitame, saccharin and cyclamates. These can also have the effect of reducing unpleasant tastes such as bitterness. Additional bitterness inhibitors or taste maskers can also be combined with active agents and sweeteners to give a reduced unpleasant taste.

Medicaments may also be combined in a coated chewing gum product. A single medicament may be added to a gum coating for fast release and also added to the gum center with or without encapsulation for slow release. If the medicament has an affinity for the gum base, it may naturally give a slow release without encapsulation. If the medicament has a fast release, it would have to be encapsulated or entrapped for the desired time release.

A combination of medicaments may be used in the gum coating and in the gum center for various reasons. In some cases, medicaments may be reactive to one another and should be kept form coming in contact with each other. In other cases, combinations of medicaments may be used for various symptoms where multiple medicaments may be effective. For example, a decongestant such as pseudoephedrine may be added to a gum coating and an antihistamine such as chlorpheniramine may be added to a gum center to treat cold/allergy symptoms. For sore throat, an oral anesthetic like dyclonine hydrochloride may be used in the gum coating and an antibacterial agent like cetyl pyridinium chloride may be added to a gum center. Additionally, any other materials like dextromethorphan hydrobromide for cough relief or an analgesic like ketoprofen may be added to a gum coating and a gum center for cold symptoms. Other combinations of medicament active agents for other types of ailments are also within the scope of this invention.

In many instances, active medicaments may have a low quality off-taste or bitterness, if added to a chewing gum coating. In most cases, this off taste may be masked with high-intensity sweeteners, but in other instances, a bitterness inhibitor may be needed to reduce a bitter taste of a medicament.

There are a wide variety of bitterness inhibitors that can be used in food products as well as with active agents. Some of the preferred bitterness inhibitors are the sodium salts that are discussed in the article *Suppression of Bitterness by Sodium: Variations Among Bitter Taste Stimuli*, by R. A. S. Breslin and G. K. Beceuchenp from Monell Chemical Senses Center, Philadelphia, Pa. Sodium salts discussed are sodium acetate and sodium gluconate. Other sodium salts that may also be effective are sodium glycinate, sodium ascorbate and sodium glycerolphosphate. Among these, the most preferred is sodium gluconate and sodium glycinate since they have a low salty taste and are most effective to reduce bitterness of most active medicaments.

Most of the sodium salts are very water-soluble and are readily released from chewing gum coating to function as bitterness inhibitors. In most instances, the sodium salts which release readily from chewing gum center may be modified by encapsulation to give an even faster release from chewing gum. However, in some instances the sodium salts would be encapsulated or entrapped to give a delayed release from gum. Generally, the bitterness inhibitor should release with the active medicament for maximum effectiveness.

Release of the medicament from gum coating may also be affected by particle size of the medicament. Small particles release more quickly whereas large particles more slowly. Fast release can also be accomplished by dissolving medicament in a liquid and used in a gum coating. Medicaments may be dissolved in solvents, flavors, or other transdermal vehicles used as absorption enhancing agents and added to gum or to a gum coating. These absorption-enhancing agents may also be added to the gum or gum coating separately from the active ingredient. Their presence may help volatilize medicaments or allow increased transmucosal absorption of the active agent through the nasal mucosa or the lungs. These solvents, flavors, or transdermal vehicles may transport medicaments faster through the oral mucosa.

Faster absorption may be affected by increasing flavor levels as well as the addition of other flavor components, such as menthol and menthol derivatives, limonene, carvone, isomenthol, eucalyptol, menthone, pynene, camphor and camphor derivatives, as well as monoterpene natural products, monoterpene derivatives, and sesquaterpenes, including caryophyllene and copaene. Other vehicles that may be used to increase transdermal absorption are: ethanol, polyethylene glycol, 2-pyrrolidones, myristic acid, Brij-35 (surfactant), p-phenyl phenol, nitrobenzene, stearyl alcohol, cetyl alcohol, croton oil, liquid paraffin, dimethyl sulfoxide (DMSO), non-ionic surfactants, liposomes, lecithin fractions, and long chain amphipathic molecules (molecules with polar or non-ionized groups on one end and non-polar groups at the other end).

In general, a chewing gum composition typically comprises a water-soluble bulk portion, a water-insoluble chewable grams base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate—vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer that is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water-soluble bulk portion and one or more flavoring agents. The water-soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, N-substituted APM derivatives such as neotame, salts of acesulfame, alitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; fructooligosaccharides (NutraFlora); palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above-described procedure may be followed.

In this invention, medicaments are preferably used in the coating/panning of a pellet chewing gum. Pellet or ball gum is prepared as conventional chewing gum but formed into pellets that are pillow shaped, or into balls. The pellets/balls can be then sugar coated or panned by conventional panning techniques to make a unique coated pellet gum. The medicament may be soluble in flavor or can be blended with powders often used in some types of conventional panning procedures. Medicaments are isolated from other gum ingredients, which modifies its release rate from chewing gum. The weight of the coating may be about 20% to about 50% of the weight of the finished product, but may be as much as 75% of the total gum product. The medicament level will usually be based on the dosage for one or two pellets.

Conventional panning procedures generally coat with sucrose, but recent advances in panning have allowed use of other carbohydrate materials to be used in place of sucrose. Some of these components include, but are not limited to, dextrose, maltose, palatinose, xylitol, lactitol, hydrogenated isomaltulose, erythritol, maltitol, and other new alditols or combinations thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth, insoluble carbonates like calcium carbonate or magnesium carbonate and talc. Antitack agents may also be added as panning modifiers, which allow the use of a variety of carbohydrates and sugar alcohols to be used in the development of new panned or coated gum products. Flavors may also be added with the sugar or sugarless coating and with the active to yield unique product characteristics.

Another type of pan coating could also incorporate the medicament (also referred to as an active agent) into a chewing gum coating. This technique is referred to as a film coating and is more common for pharmaceuticals than in chewing gum, but procedures are similar. A film like shellac, zein, or cellulose type material is applied onto a pellet-type product forming a thin film on the surface of the product. The film is applied by mixing the polymer, plasticizer and a solvent (pigments are optional) and spraying the mixture onto the pellet surface. This is done in conventional type panning equipment, or in more advanced side-vended coating pans. Since most active agents may be alcohol soluble, they may be readily added with this type of film. When a solvent like an alcohol is used, extra precautions are needed to prevent fires and explosions, and specialized equipment must be used.

Some film polymers can use water as the solvent in film coating. Recent advances in polymer research and in film coating technology eliminates the problem associated with the use of solvents in coating. These advances make it possible to apply aqueous films to a pellet or chewing gum product. Some active agents can be added to this aqueous film or even the alcohol solvent film, in which an active agent is highly soluble. This film may also contain a flavor along with a polymer and plasticizer. The active agent can also be dissolved in the aqueous or non-aqueous solvent and coated on the surface with the aqueous film. In some instances a combination of film and sugar or polyol coating may be useful, especially if the active is added with the film coating material. Also the film coating may be applied early, middle, or late in the coating process. This will give a unique release of active agent from a film-coated product.

When a coating film with an active medicament is applied to a chewing gum product, a hard shell sugar or polyol coating may then be applied over the film-coated product. In some instances a soft shell sugar or polyol coating may also be used over the film coated product. The level of film coating applied to a pellet gum may be generally from about 0.5% to about 3% of the gum product. The level of overcoating of the hard or soft shell may be about 20% to about 75%. When the active agent is added with the film coating and not with the sugar/polyol coating, better control of the amount of active agent in the product may be obtained. In addition, the sugar/polyol overcoating may give an improved stability to the active agent in the product.

As noted above, the coating may contain ingredients such as flavoring agents, as well as artificial sweeteners and dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent. Active agents may be preblended with the flavor used in coating.

Artificial sweeteners contemplated for use in the coating include but are not limited to synthetic substances, saccharin, thaumatin, alitame, saccharin salts, aspartame, N-substituted APM derivatives such as neotame, sucralose and acesulfame-K. The artificial sweetener may be added to the coating syrup in an amount such that the coating will contain from about 0.01% to about 0.5%, and preferably from about 0.1% to about 0.3% artificial sweetener.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

Coloring agents are preferably added directly to the syrup in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha (another type of acacia), alginate, cellulosics, vegetable gums and the like.

The coating is initially present as a liquid syrup which contains from about 30% to about 80% or 85% of the coating ingredients previously described herein, and from about 15% or 20% to about 70% of a solvent such as water. In general, the coating process is carried out in a rotating pan. Sugar or sugarless gum center tablets to be coated are placed into the rotating pan to form a moving mass.

The material or syrup which will eventually form the coating is applied or distributed over the gum center tablets. Flavoring agents may be added before, during and after applying the syrup to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. to about 240° F. Mostly, the syrup temperature is from about 130° F. to about 200° F. throughout the process in order to prevent the polyol (or sugar in less preferred embodiments of the invention) in the syrup from crystallizing. The preferred polyols are sorbitol and xylitol. Other polyols that dissolve rapidly may also give good results. The syrup may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup. Any number of coats may be applied to the gum center tablet. Generally, no more than about 75–100 coats are applied to the gum center tablets. The present invention contemplates applying an amount of syrup sufficient to yield a coated comestible containing about 10% to about 75% coating. Where higher dosage of an active agent is needed, the final product may be higher than 75% coating.

Those skilled in the art will recognize that in order to obtain a plurality of coated layers, a plurality of premeasured aliquots of coating syrup may be applied to the gum center tablets. It is contemplated, however, that the volume of aliquots of syrup applied to the gum center tablets may vary throughout the coating procedure.

Once a coating of syrup is applied to the gum center tablets, the present invention contemplates drying the wet syrup in an inert medium. A preferred drying medium comprises air. Forced drying air contacts the wet syrup coating in a temperature range of from about 70° to about 115° F. Generally, the drying air is in the temperature range of from about 80° to about 100° F. The invention also contemplates that the drying air possesses a relative humidity of less than about 15 percent. Preferably, the relative humidity of the drying air is less than about 8 percent.

The drying air may be passed over and admixed with the syrup coated gum centers in any way commonly known in the art. Generally, the drying air is blown over and around or through the bed of the syrup coated gum centers at a flow rate, for large-scale operations, of about 2800 cubic feet per minute. If lower quantities of material are being processed, or if smaller equipment is used, lower flow rates would be used.

For many years, flavors have been added to a sugar coating of pellet gum to enhance the overall flavor of gum. These flavors include spearmint flavor, peppermint flavor, wintergreen flavor, and fruit flavors. These flavors are generally preblended with the coating syrup just prior to applying it to the core or added together to the core in one or more coating applications in a revolving pan containing the cores. Generally, the coating syrup is very hot, about 130° to 200° F., and the flavor may volatilize if preblended with the coating syrup too early.

The concentrated coating syrup is applied to the gum cores as a hot liquid, the sugar or polyol allowed to crystallize, and the coating then dried with warm, dry air. This is repeated in about 30 to 100 applications to obtain a hard shell coated product having an increased weight gain of about 40% to 75%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these types of fruit flavors may be pretreated in order to be able to add them to a gum coating.

In an embodiment of this invention, an active agent is preblended with a gum arabic solution to become a paste and then applied to the cores. To reduce stickiness, the preblend may be mixed with a small amount of coating syrup before being applied. Forced air-drying is then continued as the gum arabic binds the active agent to the cores. Then additional coatings are applied to cover the active agent and imbed the treated active agent in the coatings.

Gum Formulation Examples

The following examples of the invention and comparative example is provided by way of explanation and illustration.

As noted earlier, the gum formulas can be prepared as sugar or sugarless type formulations. These formulas are made in a pellet or pillow shape pellet or a round ball or any other shape of product for coating/panning. However, gum formulas for pellet centers are generally adjusted to a higher flavors into the gum and more flavor is needed to give a good flavorful product. However flavors can also be added to the coating to give increased flavor impact and more flavor perception.

A wide range of changes and modifications to the embodiments of the invention described above will be apparent to persons skilled in the art. While the invention is described with respect to hard-coated chewing gum, it will be appreciated that the process is applicable to coating other food products, such as candies, in which a coating with dyclonine hydrochloride would have utility.

EXAMPLES

To illustrate the present invention, studies were performed using caffeine as a model medicament in the coating. Table 1 contains the formulas for which chewing gum centers were made.

TABLE 1

Chewing gum centers.

| | Example 1 | Example 2 | Example 3 | Example 4 | Example 5 | Example 6 |
|---|---|---|---|---|---|---|
| Base | 33.00 | 33.00 | 32.00 | 32.00 | 32.00 | 32.00 |
| Sorbitol | 46.43 | 46.05 | 39.52 | 39.02 | 38.90 | 39.02 |
| Calcium Carbonate | 13.00 | 13.00 | 15.00 | 15.00 | 15.00 | 15.00 |
| 70% Sorbitol Solution | — | — | 7.50 | 7.50 | 7.50 | 7.50 |
| Spray Dried Cooling Agent | — | — | 2.00 | 2.00 | 2.00 | 2.00 |
| Cooling Agents | — | — | 0.14 | 0.14 | 0.14 | 0.14 |
| Eucalyptus Flavor | — | — | 0.96 | 0.96 | 0.96 | 0.96 |
| Glycerin | 4.00 | 4.00 | 0.75 | 0.75 | 0.75 | 0.75 |
| Peppermint Flavor | 1.95 | 1.95 | — | — | — | — |
| Lecithin | 0.45 | 0.45 | — | — | — | — |
| Menthol | 0.35 | 0.35 | 1.26 | 1.26 | 1.26 | 1.26 |
| Encapsulated Sweeteners | 0.68 | 0.68 | 0.87 | 0.87 | 0.87 | 0.87 |
| Aspartame | 0.14 | 0.14 | — | — | — | — |
| Sodium Bicarbonate | — | 0.38 | — | 0.50 | 0.50 | — |
| Sodium Carbonate | — | — | — | — | 0.12 | 0.50 |
| Total Percentage | 100.00 | 100.00 | 100.00 | 100.00 | 100.00 | 100.00 | level of gum base than stick gum to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Even higher levels of base may be used when an active is added to a pellet coating. Generally flavors increase with the level of gum base as the base tends to bind Selected centers were coated with the coating compositions of Table 2 to a coating level of about 35% by weight of the finished, coated pellet. All pellets were formulated to contain 25 mg of caffeine in the coating.

All of the ingredients in the examples given in Table 2, except flavor and menthol, were dissolved/dispersed in hot water to create syrups of about 71 Brix (maltitol and xylitol) or about 62 Brix (sorbitol). Pellets were coated in open pans with the syrup to a final weight corresponding to 34.5% coating with the flavor/menthol preblend being added in two portions approximately one third and two thirds through the coating process.

Chewing gum coatings were made according the formulas in Table 2.

TABLE 2

Chewing gum coatings.

| Ingredient | Example 7 | Example 8 | Example 9 | Example 10 | Example 11 | Example 12 | Example 13 |
|---|---|---|---|---|---|---|---|
| Maltitol | 84.62 | — | — | — | — | — | — |
| Sorbitol | — | — | — | — | — | 89.96 | 90.88 |
| Xylitol | — | 76.47 | 76.39 | 76.01 | 84.42 | — | — |
| Caffeine* | 5.10 | 4.42 | 4.41 | 4.41 | 4.95 | 5.31 | 4.30 |

TABLE 2-continued

Chewing gum coatings.

| Ingredient | Example 7 | Example 8 | Example 9 | Example 10 | Example 11 | Example 12 | Example 13 |
|---|---|---|---|---|---|---|---|
| Gum Acacia** | 7.90 | — | — | — | — | — | — |
| Gum Talha** | — | 17.64 | 17.61 | 17.61 | 8.98 | 3.64 | 3.68 |
| Menthol | 0.67 | 0.35 | 0.35 | 0.35 | 0.37 | 0.08 | 0.06 |
| Titanium Dioxide | 0.60 | 0.45 | 0.45 | 0.45 | 0.50 | 0.77 | 0.78 |
| Peppermint Flavor | 0.54 | 0.67 | 0.67 | 0.67 | 0.11 | 0.24 | 0.18 |
| Aspartame | 0.27 | — | — | — | — | — | — |
| Talc | 0.16 | — | — | — | — | — | — |
| Cooling Agents | 0.13 | — | — | — | — | — | — |
| Sodium Bicarbonate | — | — | — | 0.50 | 0.67 | — | — |
| Sodium Carbonate | — | — | 0.12 | — | — | — | 0.12 |
| Total % | 100.00 | 100.00 | 100.00 | 100.00 | 100.00 | 100.00 | 100.00 |

*Added to hot water first to completely dissolve.
**Added as a 40% solution in water.

Six volunteers chewed two pellets of each product for 20 minutes, expectorating and collecting all saliva produced during the chew. After chewing, the cud was collected and analyzed along with the collected saliva for caffeine content. The difference between the initial caffeine content and the recovered caffeine (i.e. unrecovered caffeine) was presumed to have been absorbed through the oral mucosa. These data are summarized in Table 3.

caffeine, and therefore presumably absorption, from 3 to 7%. The addition of bicarbonate to the center in xylitol coated gums (Examples 16 and 17) and to the center in sorbitol coated gums (Examples 18 and 19) had the same benefit, increased percentages of unrecovered caffeine. Also, compared to the malitol coated gum products (Examples 14 and 15) both the xylitol (Examples 16 and 17) and sorbitol (Examples 18 and 19) coatings gave dramatically increased

TABLE 3

Chewing gums used in experimental trials

| Example No. | Center | Coating | Water-Soluble Alkaline Material in Center | Water-Soluble Alkaline Material in Coating | % Water-Soluble Alkaline Material of Total Wt. | % Unrecovered Caffeine ± SD |
|---|---|---|---|---|---|---|
| 14* | Example 1 | Example 7 Maltitol | 0 | 0 | 0 | 3 ± 4 |
| 15 | Example 2 | Example 7 Maltitol | 0.38% NaHCO$_3$ | 0 | 0.25 | 7 ± 6 |
| 16 | Example 3 | Example 8 Xylitol | 0 | 0 | 0 | 31 ± 14 |
| 17 | Example 4 | Example 8 Xylitol | 0.50% NaHCO$_3$ | 0 | 0.32 | 39 ± 5 |
| 18 | Example 3 | Example 12 Sorbitol | 0 | 0 | 0 | 32 ± 8 |
| 19 | Example 4 | Example 12 Sorbitol | 0.50% NaHCO$_3$ | 0 | 0.33 | 47 ± 6 |
| 20 | Example 3 | Example 9 Xylitol | 0 | 0.12% Na$_2$CO$_3$ | 0.04 | 22 ± 9 |
| 21 | Example 5 | Example 9 Xylitol | 0.50% NaHCO$_3$ 0.12% Na$_2$CO$_3$ | 0.12% Na$_2$CO$_3$ | 0.43 | 34 ± 10 |
| 22 | Example 3 | Example 13 Sorbitol | 0 | 0.12% Na$_2$CO$_3$ | 0.04 | 34 ± 6 |
| 23 | Example 4 | Example 13 Sorbitol | 0.50% NaHCO$_3$ | 0.12% Na$_2$CO$_3$ | 0.37 | 43 ± 8 |
| 24 | Example 6 | Example 8 Xylitol | 0.50% Na$_2$CO$_3$ | 0 | 0.33 | 31 ± 8 |
| 25 | Example 3 | Example 10 Xylitol | 0 | 0.50% NaHCO$_3$ | 0.17 | 35 ± 8 |

*Example 14 is a comparative example.

The table above summarizes the results of screening performed to determine the level of unrecovered caffeine from the gums. The results indicated that in maltitol coated gums, adding sodium bicarbonate to the center (Examples 14 and 15) increased average percentages of unrecovered percentages of unrecovered caffeine, going from 3–7% up to 31–39% and 32–47%. When 0.12% sodium carbonate was added to the coating, neither xylitol nor sorbitol coated gum demonstrated significantly increased levels of unrecovered caffeine (22% and 34% respectively), when compared to either gum without the sodium carbonate in the coating. This may be attributed to the lower percentage of sodium bicarbonate to the entire product as compared to the percentage of sodium bicarbonate present when it is added to the gum center. It is believed that adding a higher level of sodium bicarbonate to the gum coating will also provide absorption enhancement of a medicament through the oral mucosa.

In Table 3, Example No. 15 contains sodium bicarbonate in the gum center with a maltitol coating. Example No. 17 contains sodium bicarbonate in the gum center with a xylitol coating. The % caffeine unrecovered, presumably absorbed by the chewer of the product, was 7±6 for Example No. 15 and was 39±5 for Example No. 17. There is a clear benefit of caffeine absorption with the sodium carbonate in the gum center with a xylitol coating. If Example No. 17 is then compared to Example No. 21, which contains sodium bicarbonate and carbonate in the gum center with a xylitol coating which also contains sodium carbonate, there is no clear benefit of having the sodium carbonate in the xylitol coating, as the % caffeine unrecovered for Example No. 21 was 34±10. If Example No. 15 again is compared to Example No. 19, which is a gum center with sodium bicarbonate and a sorbitol coating, the % caffeine unrecovered for Example No. 19 is 47±6, showing a clear benefit over the maltitol coating.

Plasma studies were also performed using three separate extractions and analyses performed on the caffeine gum pellets. Data from six subjects participating in each study were compiled. The gum samples were chewed, all saliva expectorated, gum cud retained, and saliva and gum cud analyzed for caffeine levels. The level of caffeine unrecovered when compared to the theoretical level present, was presumed to be the level of caffeine absorbed through the oral cavity. Results of the experimental gum were averaged and compared to results from the control gum.

bonate gum than after chewing the xylitol gum. This correlates to faster caffeine absorption in the bloodstream, meeting the objective of the invention.

In addition to completing the goal, these data demonstrated how chew and expectorate tests can be used to predict which gum formulations will perform significantly better in plasma trials. Example No. 19 was tested in chew and expectorate trials vs. the Example No. 16. The gum of Example No. 19 demonstrated a significantly greater level of unrecovered caffeine in the chew and expectorate trial when compared to Example No. 16 gum. In plasma trials, this gum also demonstrated significantly greater levels of plasma caffeine absorption.

The gum of Example No. 23, found in Table 3, demonstrated higher level of unrecovered caffeine in the chew and expectorate trial when compared to the xylitol coated gum, Example No. 16, and also demonstrated a greater level of plasma caffeine absorption. These data indicate that the chew and expectorate trial is a valid screener and can be used to help predict how a gum will perform in a plasma trial.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes that come within the meaning and range of equivalency of the claims are to be embraced within their scope.

TABLE 4

| Gum samples used in Plasma Trials | |
|---|---|
| Gum Sample | Caffeine Level Per Pellet |
| Example No. 16 from Table 3 | 25 mg × 2 pellets. 95% chewed-out after 10 minutes, dosage 46–50 mg. Caffeine per trial approximately 50 mg. |
| Example No. 23 from Table 3 | 31 mg × 2 pellets, approximately 93% chewed-out after 10 minutes, dosage 57–62 mg. Caffeine per trial approximately 62 mg. |
| Example No. 19 from Table 3 | 20 mg × 2 pellets, approximately 93% chewed-out after 10 minutes, dosage 37–40 mg. Caffeine per trial approximately 40 mg. |

For N=6 test subjects, average caffeine plasma absorption rate constant was significantly greater from Example No. 19 (sorbitol coating with bicarbonate in center) (0.092) than from the Example No. 16 (xylitol coating and no bicarbonate) (0.057), (95% significance). This indicates that the caffeine was released into the bloodstream at a faster rate after chewing the sorbitol coated bicarbonate gum than after chewing the xylitol coated gum. This correlates to faster caffeine absorption in the bloodstream, meeting the objective of the invention. Preferably the medicament will be delivered at a rate greater than 30% more than the rate that the medicament would have been delivered if the bicarbonate were not present.

For N=6 test subjects, the average caffeine plasma absorption ½ life (which is the time it takes for the concentration of caffeine in the plasma to reach one-half its peak amount) was significantly lower for Example No. 19 (8.51 minutes) than the Example No. 16 (13.84 minutes), (95% significance). This indicates that ½ the peak plasma caffeine level is reached more quickly after chewing the sorbitol/bicar-

What is claimed is:

1. A coated chewing gum product with absorption acceleration of a medicament, comprising:
   a) a chewing gum center comprising a gum base, a flavor, and a bulking/sweetening agent;
   b) a chewing gum coating comprising a polyol selected from the group consisting of xylitol and sorbitol, and containing at least one medicament; and
   c) a bicarbonate salt incorporated into the chewing gum center, the coating, or both.

2. The coated chewing gum product of claim 1 wherein the bicarbonate salt comprises from about 0.1% to about 1% by weight of the chewing gum product.

3. The coated chewing gum product of claim 1 wherein said bicarbonate salt is sodium bicarbonate.

4. The coated chewing gum product of claim 3 wherein the amount of said sodium bicarbonate ranges from 0.2% to 0.7% by weight of the chewing gum product.

5. The coated chewing gum product of claim 3 wherein said sodium bicarbonate is in the chewing gum center.

6. The coated chewing gum product of claim 3 wherein said sodium bicarbonate is present in the coating.

7. The coated chewing gum product of claim 3 wherein said sodium bicarbonate is present in both the chewing gum center and the coating.

8. The coated chewing gum product of claim 1 wherein said bulking/sweetening agent comprises a high-intensity sweetener selected from the group consisting of aspartame, alitame, salts of acesulfame, cyclamate and its salts, saccharine and its salts, neotame, thaumatin, monellin, dihydrochalcones, sucralose and combinations thereof.

9. The coated chewing gum product of claim 1 wherein said gum center further comprises a cooling agent.

10. The coated chewing gum product of claim 1 wherein said gum center further comprises a plasticizing agent.

11. The coated chewing gum product of claim 1 wherein said coating comprises at least one flavor.

12. The coated chewing gum product of claim 1 wherein said medicament comprises an orally administrable medicament selected from a group consisting of stimulants, vitamins, minerals, herbal supplements, neutraceuticals, nicotine, nicotine replacement agents, antacids, analgesics and combinations thereof.

13. The chewing gum product of claim 1 wherein said medicament comprises an orally administrable medicament selected from the group consisting of tranquilizers, cardiovascular agents, cancer therapeutics, anitmycotics, oral contraceptives, muscle relaxants, antihistamines, decongestants, antibacterial agents, anesthetics, antitussives, diuretics, anti-inflammatories, HIV medications, AIDS medications, neurological drugs, antivirals, psychotherapeutic agents, anti-diabetic agents and combinations thereof.

14. The coated chewing gum product of claim 1 wherein said chewing gum coating comprises xylitol and the bicarbonate salt comprises sodium bicarbonate incorporated into the chewing gum center.

15. The coated chewing gum product of claim 1 wherein said chewing gum coating comprises sorbitol and the bicarbonate salt comprises sodium bicarbonate incorporated into the chewing gum center.

16. A coated chewing gum product including a medicament comprising:
a) a chewing gum center;
b) a chewing gum coating containing at least one medicament and a polyol selected from the group consisting of xylitol and sorbitol; and
c) a bicarbonate salt incorporated into the chewing gum center, the coating, or both.

17. The coated chewing gum product of claim 16 wherein said bicarbonate salt is sodium bicarbonate.

18. The coated chewing gum product of claim 17 wherein the amount of said sodium bicarbonate ranges from 0.1% to 1% by weight of the entire product.

19. The coated chewing gum product of claim 16 wherein said water-soluble alkaline material is in the chewing gum center.

20. The coated chewing gum product of claim 16 wherein said bicarbonate salt is present in the coating.

21. The coated chewing gum product of claim 16 wherein said bicarbonate salt is present in both the chewing gum center and the coating.

22. The coated chewing gum product of claim 16 wherein said chewing gum center comprises a high-intensity sweetener selected from the group consisting of aspartame, alitame, salts of acesulfame, cyclamate and its salts, saccharine and its salts, neotame, thaumatin, monellin, dihydrochalcones, sucralose and combinations thereof.

23. The coated chewing gum product of claim 16 wherein said coating comprises least one flavor.

24. The chewing gum product of claim 16 wherein said medicament comprises an orally administrable medicament selected from a group consisting of stimulants, vitamins, minerals, herbal supplements, neutraceuticals, nicotine, nicotine replacement agents, antacids, analgesics and combinations thereof.

25. The chewing gum product of claim 16 wherein said medicament comprises an orally administrable medicament selected from the group consisting of tranquilizers, cardiovascular agents, cancer therapeutics, anitmycotics, oral contraceptives, muscle relaxants, antihistamines, decongestants, antibacterial agents, anesthetics, antitussives, diuretics, anti-inflammatories, HIV medications, AIDS medications, neurological drugs, antivirals, psychotherapeutic agents, anti-diabetic agents and combinations thereof.

26. The coated chewing gum product of claim 16 wherein said medicament comprises an encapsulated medicament.

27. The coated chewing gum product of claim 16 wherein said medicament comprises caffeine.

28. A method of delivering a medicament with accelerated absorption through the oral mucosa comprising the steps of:
a) providing a chewing gum center;
b) coating the chewing gum center with a coating comprising a polyol selected from the group consisting of xylitol and sorbitol, and containing at least one medicament;
c) either the chewing gum center, the coating, or both incorporating a bicarbonate salt; and
d) causing an individual in need of the medicament to chew the product.

29. The method of claim 28 wherein said bicarbonate salt is sodium bicarbonate.

30. The method of claim 29 wherein the amount of said sodium bicarbonate ranges from 0.1% to 1% by weight of the chewing gum product.

31. The method of claim 28 wherein said medicament comprises an orally administrable medicament selected chosen from a group consisting of stimulants, vitamins, minerals, herbal supplements, neutraceuticals, nicotine, nicotine replacement agents, antacids, analgesics and combinations thereof.

32. The method of claim 28 wherein said medicament comprises an orally administrable medicament selected from the group consisting of tranquilizers, cardiovascular agents, cancer therapeutics, anitmycotics, oral contraceptives, muscle relaxants, antihistamines, decongestants, antibacterial agents, anesthetics, antitussives, diuretics, anti-inflammatories, HIV medications, AIDS medications, neurological drugs, antivirals, psychotherapeutic agents, anti-diabetic agents and combinations thereof.

33. The method of claim 28 wherein said medicament comprises an encapsulated medicament.

34. The method of claim 28 wherein said medicament comprises caffeine.

35. The method of claim 28 wherein the medicament is delivered at a rate greater than 30% more than the rate that the medicament would have been delivered if the bicarbonate salt were not present.

36. A coated chewing gum product with absorption acceleration of caffeine, comprising:
a) a chewing gum center comprising a gum base, a flavor, and a bulking/sweetening agent;
b) a chewing gum coating comprising caffeine and a polyol selected from the group consisting of sorbitol and xylitol; and
c) a bicarbonate salt incorporated into the chewing gum center, the coating, or both.

* * * * *